United States Patent [19]
Errico et al.

[11] Patent Number: 5,725,588
[45] Date of Patent: *Mar. 10, 1998

[54] ACETABULAR CUP HAVING POLYAXIAL LOCKING SCREWS

[75] Inventors: Joseph P. Errico, Far Hills; Thomas J. Errico, Summit; James D. Ralph, Oakland, all of N.J.

[73] Assignee: Fastenetix, LLC, Summit, N.J.

[*] Notice: The term of this patent shall not extend beyond the expiration date of Pat. No. 5,520,690.

[21] Appl. No.: 632,560

[22] Filed: Apr. 15, 1996

Related U.S. Application Data

[63] Continuation-in-part of Ser. No. 421,087, Apr. 13, 1995, Pat. No. 5,520,690.

[51] Int. Cl.⁶ .................................................. A61F 2/28
[52] U.S. Cl. .................................. 623/22; 606/86
[58] Field of Search ............................ 606/69, 70, 71, 606/61, 60, 72, 73; 623/22, 23, 18

[56] References Cited

U.S. PATENT DOCUMENTS

| | | | |
|---|---|---|---|
| 4,936,861 | 6/1990 | Muller et al. | 623/22 |
| 5,376,125 | 12/1994 | Winkler | 623/23 |
| 5,443,467 | 8/1995 | Biedermann et al. | 606/65 |
| 5,474,555 | 12/1995 | Puno et al. | 606/73 |
| 5,514,184 | 5/1996 | Doi et al. | 623/23 |
| 5,520,690 | 5/1996 | Errico et al. | 606/61 |
| 5,534,027 | 7/1996 | Hodorek | 623/16 |
| 5,607,426 | 3/1997 | Ralph et al. | 606/61 |

Primary Examiner—Guy V. Tucker
Attorney, Agent, or Firm—Joseph P. Errico, Esq.

[57] ABSTRACT

The present invention is an acetabular cup having polyaxial locking screws for anchoring the cup in the desired bone site. The assembly includes an acetabular cup having axially tapered holes, into which holes coupling elements and bone screws may be inserted. The coupling elements each have an axial taper which matches the taper of the corresponding hole, and an interior semi-spherical concave surface in which the semi-spherical head of a corresponding bone screw may be polyaxially mounted. The bone screws are inserted through the holes until the coupling elements fully seat in the respective holes, thereby locking the screws in place and the coupling elements in the holes. In a preferred embodiment, the upper part of the holes further include annularly recessed channels in each of which a snap-ring is disposed. During the insertion of the bone screw, the advancing of the coupling element into the hole causes the snap-ring to expand. Once the coupling element is fully seated in the hole, the snap-ring contracts to its undeflected position and prevents the coupling element and screw from backing out of the hole in the event of loosening.

9 Claims, 7 Drawing Sheets

ACETABULAR CUP HAVING POLYAXIAL LOCKING SCREWS

CROSS REFERENCE TO A RELATED APPLICATION

This application is a continuation-in-part of application U.S. Ser. No. 08/421,087, entitled "Anterior Spinal Polyaxial Locking Screw Plate Assembly", filed Apr. 13, 1995, now U.S. Pat. No. 5,520,690.

BACKGROUND OF THE INVENTION

1. Field of the Invention

This invention relates generally to a replacement hip implant assembly, and more specifically to an acetabular cup having a plurality of tapered holes therein for receiving polyaxial locking screws and coupling elements, such that the screws may be inserted into the adjacent bone at a wide range of angles.

2. Description of the Prior Art

Hip implant devices, which are utilized to replace corresponding degenerated joints, generally include an outer metal cup (acetabular cup), and inner polymer or ceramic cup, a metal or ceramic ball, and a femoral post. The outer metal cup is implanted into the acetabulum (the socket portion of the pelvis), and secured therein by a variety of means, some of which are described hereinbelow. The inner polymer or ceramic cup seats within the outer metal cup and has a smooth semi-spherical interior conformation for receiving the metal or ceramic ball. The ball is smooth so as to provide low-friction polyaxially rotatability within the semi-spherical interior of the inner cup. The ball is also coupled to the top of the femoral post, which extends into the top of the femur to complete the coupling of the hip to the femur, while permitting rotation of the artifial joint.

There are a number of prosthetic hip devices which have been disclosed in the art which include the elements set forth above in various embodiments. The various embodiments disclose a spectrum of means for securing the acetabular cup to the pelvis. Some teach integral projections extending from the exterior surface of the cup-shaped body which provide anchoring for the element within the surrounding bone. European Patent Application No. 13,863, published on Jun. 8, 1980 describes such a device. The cup of this reference is anchored to the bone by a central pin and a number of other pins distributed over the surface of the cup. The pins have sawtooth notches along their length and are inserted into pre-drilled holes in the bone. Similarly, European Patent Application No. 211,169 published Feb. 25, 1987, discloses an acetabular cup which includes an external boss protruding from the outer surface of the cup to fit into a pre-drilled hole in the acetabulum.

An advance over fixed and integral anchoring projections is illustrated in U.S. Pat. No. 4,828,565 wherein the acetabular shell includes a pair of outwardly projecting elements which are fixed, but through which screws may be passed to further secure the cup in the bone.

The use of screws alone to anchor the acetabular cup in the surrounding bone is described in U.S. Pat. Nos. 3,939,497 and 4,685,923 in which a series of radially arranged pegs may be selectively projected outwardly through the wall of the cup into the surrounding bone.

In each of the devices described above, the integral anchoring projections and/or the selectively introduceable screws, the entrance angles of the securing means are rigidly predetermined. As it is desirable to provide the surgeon with the freedom to choose the entrance angle of the screw to best suit the individual conformation of the surrounding bone on a patient-by-patient basis, U.S. Pat. No. 4,792,337 provides an acetabular cup having countersunk holes and screws having rounded heads, such that the orientation of the screws may be varied with respect to the cup and each other.

While it is a substantial gain over the previous designs to provide for variability in screw entrance angle, a common concern with screws being implanted into bone is that the screws may dislocate and begin a process known as "pull-out". This is an especially important problem in conjunction with acetabular cups, wherein dislocated screws often impede the rotational motion of the device and/or provide a wearing impetus to erode the low friction surfaces at the motion interface.

There are no presently available screw plate assemblies which present a flush surface and provide for means of preventing both screw pull-out from the bone and screw backout, while simultaneously providing for a wide range of angulation for the bone screws.

It is therefore, an object of the present invention to provide a new and novel acetabular cup and anchoring screw design which allows for polyaxial entrance of the screw into the surrounding bone.

It is also an object of the present invention to provide an orthopaedic implant which has a simple and effective mechanism for locking the bone screw to the acetabular cup.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a locking polyaxial screw and coupling element assembly for use in anchoring acetabular cups within surrounding bone tissue. The assembly comprises: an acetabular cup having a plurality of tapered holes; bone screws having semi-spherical heads; and corresponding coupling elements. In a preferred embodiment, the tapered holes include a retaining snap-ring to further prevent screw back-out.

The acetabular cup of this invention is generally of a type which is well known in the art, having a semi-spherical exterior conformation for insertion into the prepared bone site, and a curvate interior wherein the inner cup of the device is disposed. The cup further includes a plurality of holes extending through the cup; each of the holes having an axial taper such that the hole is wider at the interior surface of the cup than at the exterior thereof.

The heads of the screws further comprise a recessed region such as a slot, phillips, star, or hexagonal recesses which are ideally suited for mating to an appropriate screw-driving tool. The recess, however, does not alter the exterior radially semi-spherical shape of the head.

The coupling elements have tapered external surfaces which match the taper of the corresponding through holes. Each coupling element further includes an interior volume which is semi-spherical to polyaxially retain the semi-spherical head of the corresponding screw. The coupling elements are axially slotted with one or more slots such that a radially applied force causes the interior volume to expand or contract according to the direction of the applied force. This expansion permits the head of the screw to be inserted into the interior volume; and the contraction provides for the crush locking of the interior surface of the coupling element to the head of the screw. Prior to use, each coupling element is joined with a corresponding screw. The coupling element must provide a recess or opening in the top thereof so that the screw and coupling element may be manipulated easily so that the recess in the head of the screw is accessible.

The first step in the process of implanting this invention is to position the acetabular cup in the properly formed recess of the pelvis and to align the entry points for the screws. Next, pre-drilled holes are formed in the surrounding bone at the desired angle, into which the anchoring bone screws are to be inserted. With the cup in place, the screws are inserted through the holes. Once a given screw has been inserted into the bone, at the desired angle, the coupling element, via its rotationally free mating to the inserted screw, is realigned so that it seats into the hole. Continued screwing down causes the bottom of the coupling element to advance into the hole.

The final seating of the coupling element in the depth of the tapered hole causes the element to contract slightly (as the axial slot or slots are narrowed). This contraction causes the interior volume to crush-lock to the semi-spherical head of the screw thereby locking it at the given angulation. Simultaneously, the coupling element is expansion locked to the inner surface of the hole by friction.

In the preferred embodiment, wherein the tapered holes further include retaining snap-rings, the snap-rings are disposed in annular recessed channels in the portions of the tapered sidewall of the holes closest to the inner surface of the cup. The snap-ring, itself, is a flat, circumferentially discontinuous, circular element. The discontinuity in the element permits the ring to be radially compressed for placement in the channel, and also to be expanded to permit the tapered coupling element to slide through it deeper into the hole. After the coupling element passes through it, however, the ring snaps back into its undeflected shape which fits loosely in the recessed channel, and extends radially inward to block the element from backing out of the hole, by interference.

DETAILED DESCRIPTION OF THE PREFERRED EMBODIMENT

While the present invention will be described more fully hereinafter with reference to the accompanying drawings, in which particular embodiments and methods of fabrication are shown, it is to be understood at the outset that persons skilled in the art may modify the invention herein described while achieving the functions and results of this invention.

Accordingly, the descriptions which follow are to be understood as illustrative and exemplary of specific structures, aspects and features within the broad scope of the present invention and not as limiting of such broad scope. Like numbers refer to similar features of like elements throughout.

Figure 1:
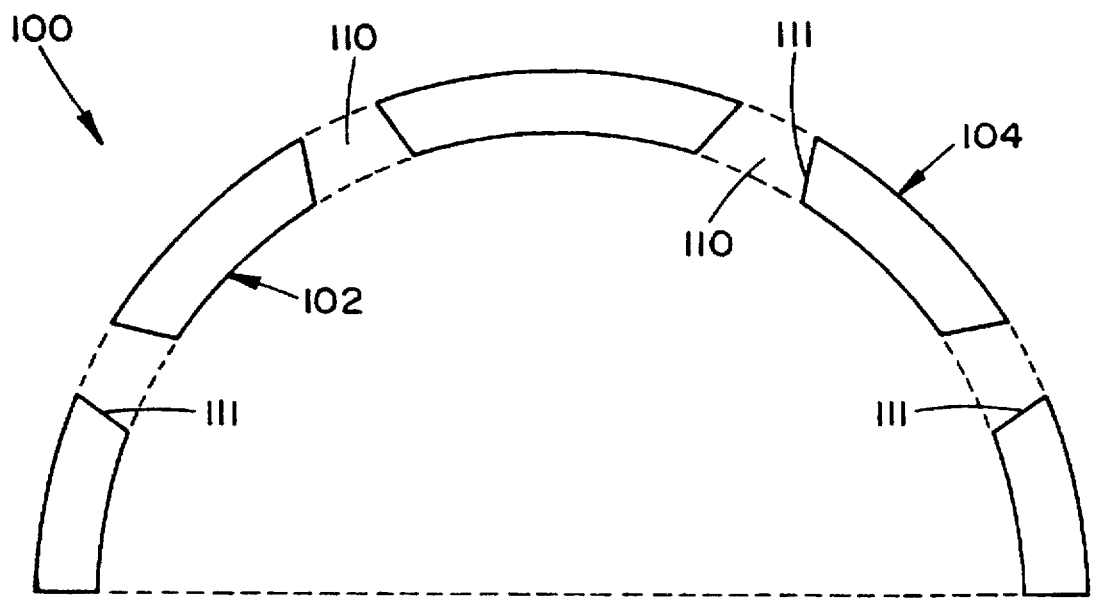
FIG. 1 is a side cross-section view of an acetabular cup which is an aspect of the present invention.
Figure 2:
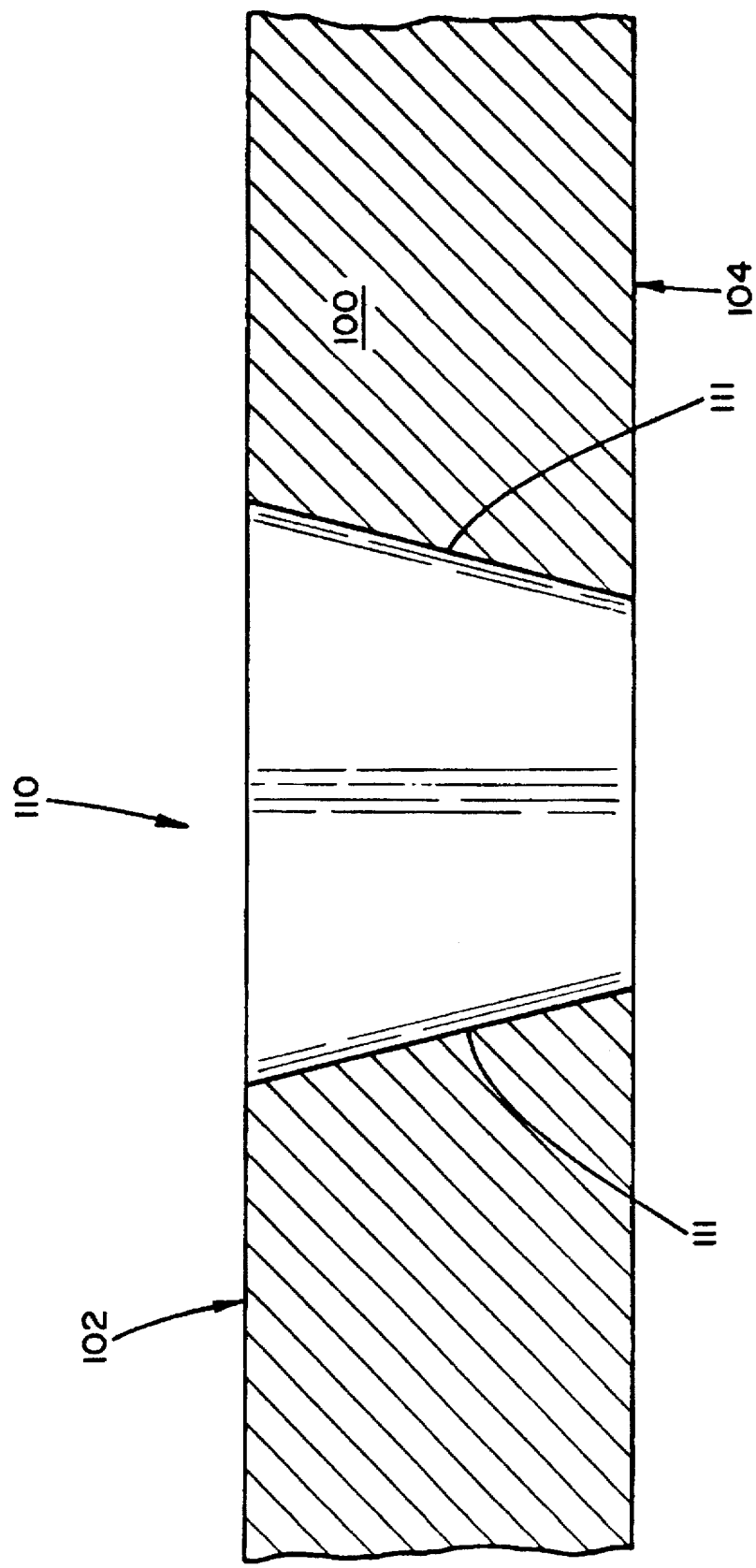
FIG. 2 is a side cross-section view of an axially tapered hole of the present invention.

Referring now to FIGS. 1 and 2, an acetabular cup 100 of the present invention is shown, respectively, in a side cross-section view, the cross-section being taken in a diametric plane, and a side cross-section of one of the axially tapered holes 110 therein. The cup 100 may be constructed of any suitably biocompatible material which has the structural strength and durability to withstand the cyclical loading associated with long term fixation in the hip. Materials which would be suitable for such applications include titanium alloys and steels. A specific titanium material which has been utilized in implants of the prior art include 316 stainless steel. This material has enhanced mechanical properties including fatigue endurance and tensile strength, as compared with other materials.

The cup 100 comprises inner and outer surfaces 102, 104, said inner surface 102 being concave and the outer surface 104 being convex. A second cup shaped insert (not shown) is often affixed within the acetabular cup 100, the inner surface of this second cup being the bearing surface against which the ball head of the femoral post portion of the artificial hip joint rotates.

A plurality of holes 110, having a smooth tapered inner surface 111, extend fully through the cup 100. Each of the holes 110 is ideally suited for receiving therethrough a bone screw for affixing the plate to the vertebral bodies.

Figure 3:
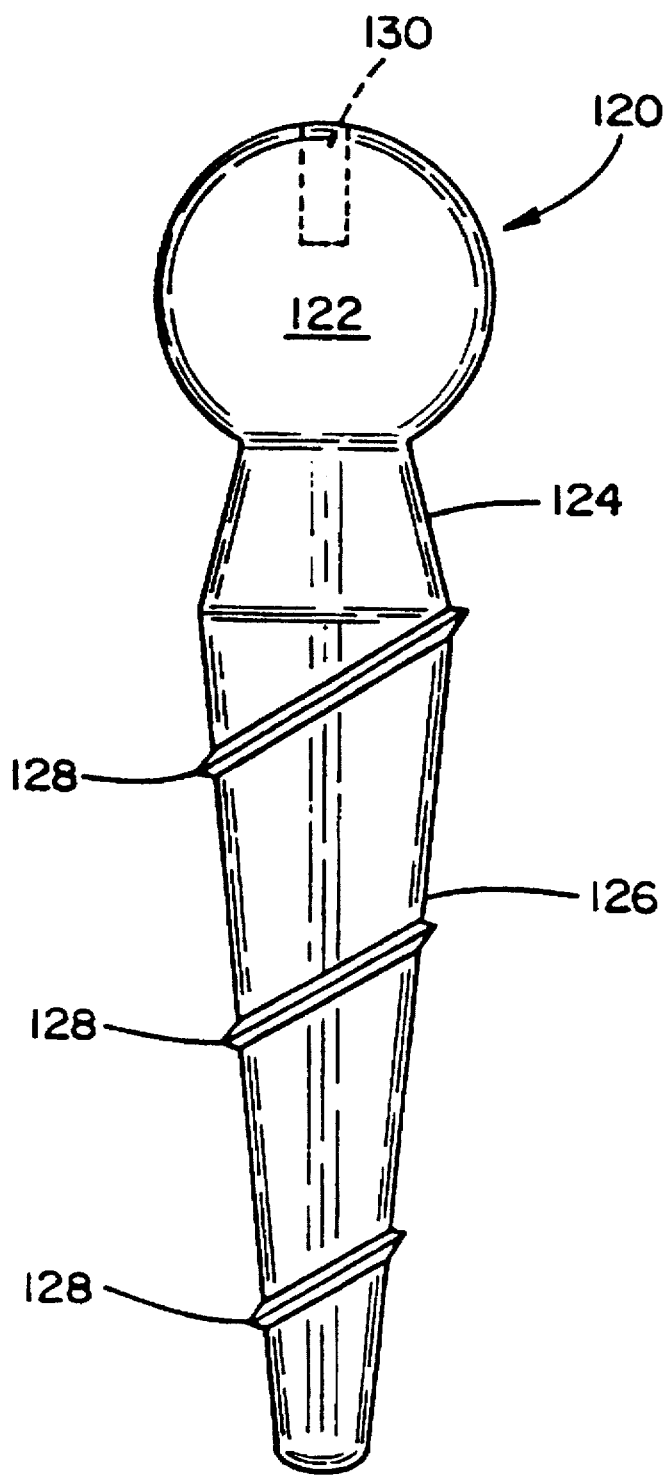
FIG. 3 is a side view of a bone screw of the present invention.

Referring now to FIG. 3, a screw of a type which is ideally suited for securing the acetabular cup 100 of this invention to the hip of the patient is shown in a side view. The screw 120 comprises a head portion 122, a neck 124, and a shaft 126. In FIG. 3, the shaft 126 is shown as having a tapered shape with a high pitch thread 128. It shall be understood that a variety of shaft designs are interchangeable with the present design. The specific choice of shaft features, such as thread pitch, or shaft diameter to thread diameter ratio, or overall shaft shape, etc. should be made be the physician with respect to the conditions of the patient's bone, however, this invention is compatible with a wide variety of shaft designs.

The head portion 122 of the screw 120 comprises a semi-spherical shape, which has a recess 130 in it. It is understood that the semi-spherical shape is necessarily is a section of a sphere, greater in extent than a hemisphere, and exhibits an external contour which is equidistant from a center point of the head. In a preferred embodiment, the major cross-section of the semi-spherical head 122 (as shown in the two dimensional illustration of FIG. 3) includes at least 270 degrees of a circle.

The recess 130 defines a receiving locus for the application of a torque for driving the screw 120 into the bone. The specific shape of the recess 122 may be chosen to cooperate with any suitable screwdriving tool. For example, the recess 130 may comprise a slot for a flat-headed screwdriver, a crossed recess for a phillips head screwdriver, a hexagonally shaped hole for receiving an allen wrench, or most preferably, a threading for receiving a correspondingly threaded post. It is further preferable that the recess 130 be co-axial with the general elongate axis of the screw 120, and most particularly with respect to the shaft 126. Having the axes of the recess 130 and the shaft 126 co-linear facilitates the step of inserting the screw 120 into the bone.

The semi-spherical head portion 122 is connected to the shaft 126 at a neck portion 124. While it is preferable that the diameter of the shaft 126 be less than the radius of the semi-spherical head 122, it is also preferable that the neck 124 of the screw 120 be narrower than the widest portion of the shaft 126. This preferable dimension permits the screw to be inserted at a variety of angles while still permitting the specific coupling element to be screwed into the appropriate hole 110 or 112 of the plate 100 and remain coupled to the head 122.

Figure 4:
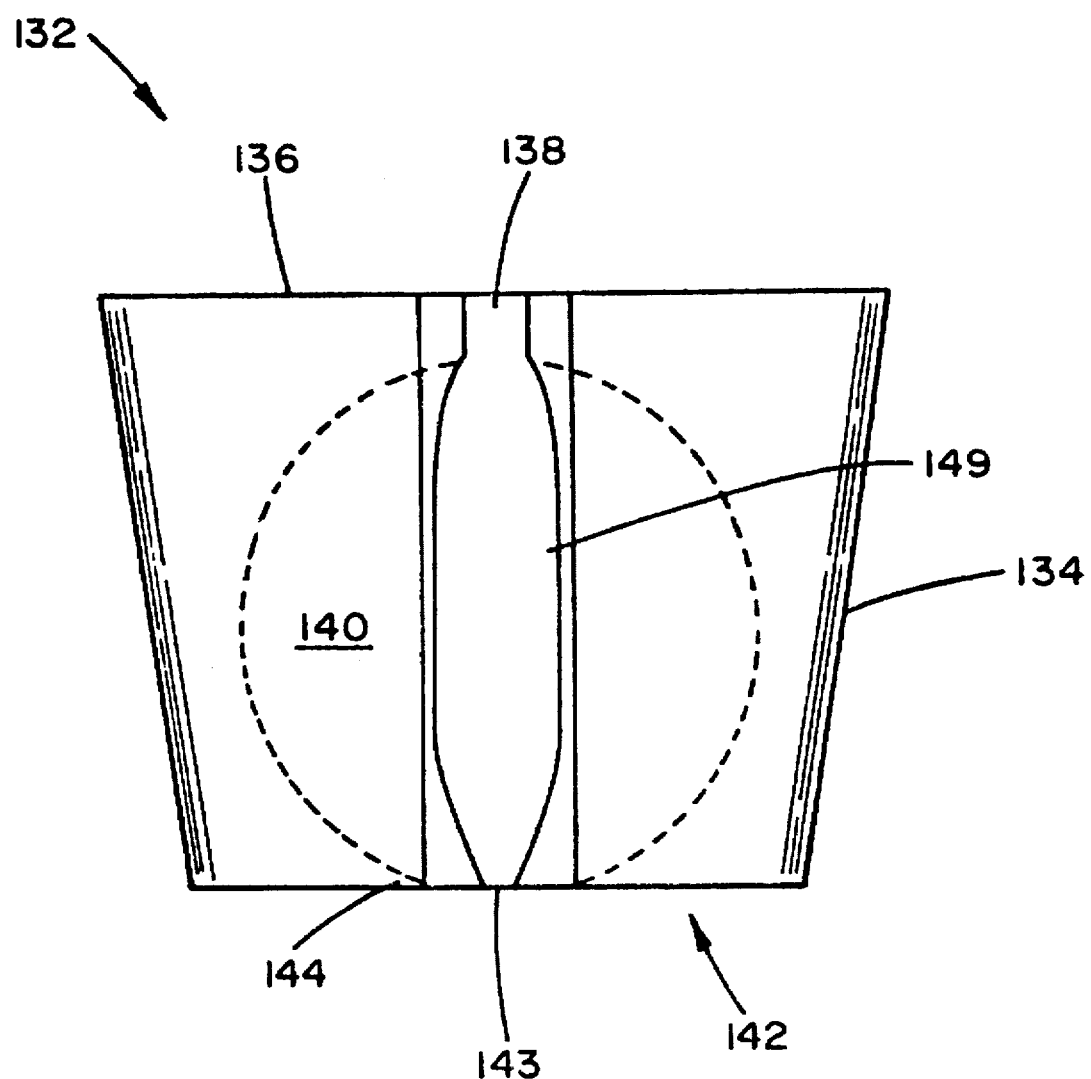
FIG. 4 is a side view of the coupling element which receives the bone screw as shown in FIG. 3.

Referring now also to FIG. 4 the coupling element 132, which is utilized in conjunction with the acetabular cup 100 shown in FIG. 1, is shown in a side view, wherein phantom lines show the interior structure of the element along a diametrical cross-section. The coupling element 132 comprises a tapered cylindrical socket having a smooth external surface 134. The taper of the surface 134 is designed to mate with the interior tapered surface 111 of the holes 110 of the cup 100, so that the coupling element 132 may be seated into the holes 100.

The top surface 136 of the coupling element 132 further comprises a through hole 138, which extends from the top surface 136 to an interior semi-spherical volume 140. This through hole 138 is designed such that the screwdriving tool which is used to insert the screw 120 into the bone may access and rotate the screw 120 through the coupling element.

The coupling element 132 further includes an interior semi-spherical volume 140 which is ideally suited for holding the head portion 122 of the screw 120, and permitting the screw to rotate through a range of angles. The bottom 142 of the coupling element 132 has a circular hole (enumerated as 143 on the bottom surface of the side view of the coupling element) which forms the bottom entrance into the interior semi-spherical volume 140. It is understood that the head 122 of the screw 120 is held within the interior semi-spherical volume 140 by the annular rim, or support lip, 144 of the bottom 142 of the coupling element. This annular support lip 144 defines the circular opening 143 which has a diameter less than the diameter of the semi-spherical head 122 of the screw 120, but larger than the neck 124 of the screw 120 (so that the screw 120 may polyaxially rotate relative to the coupling element 132 once the head 122 has been inserted into the interior volume 140.

The coupling element 132 may comprise a plurality of axial slots which extend axially upward part of the way from the bottom of the element to the top, however, in a preferred embodiment, the element 132 comprises a single axial slot 149 which extends fully up the element 132 so that it has a circumferentially discontinuous conformation. This renders the coupling element 132 a ⅞ths collar, and permits the element 132 to expand to accept the inserted head portion 122, and also to crush against the head 122 upon the application of an inwardly directed radial force. Insertion of the coupling elements into the through holes prevents the coupling elements from releasing the head 122 by preventing the circular opening 143 from expanding.

Figure 5:
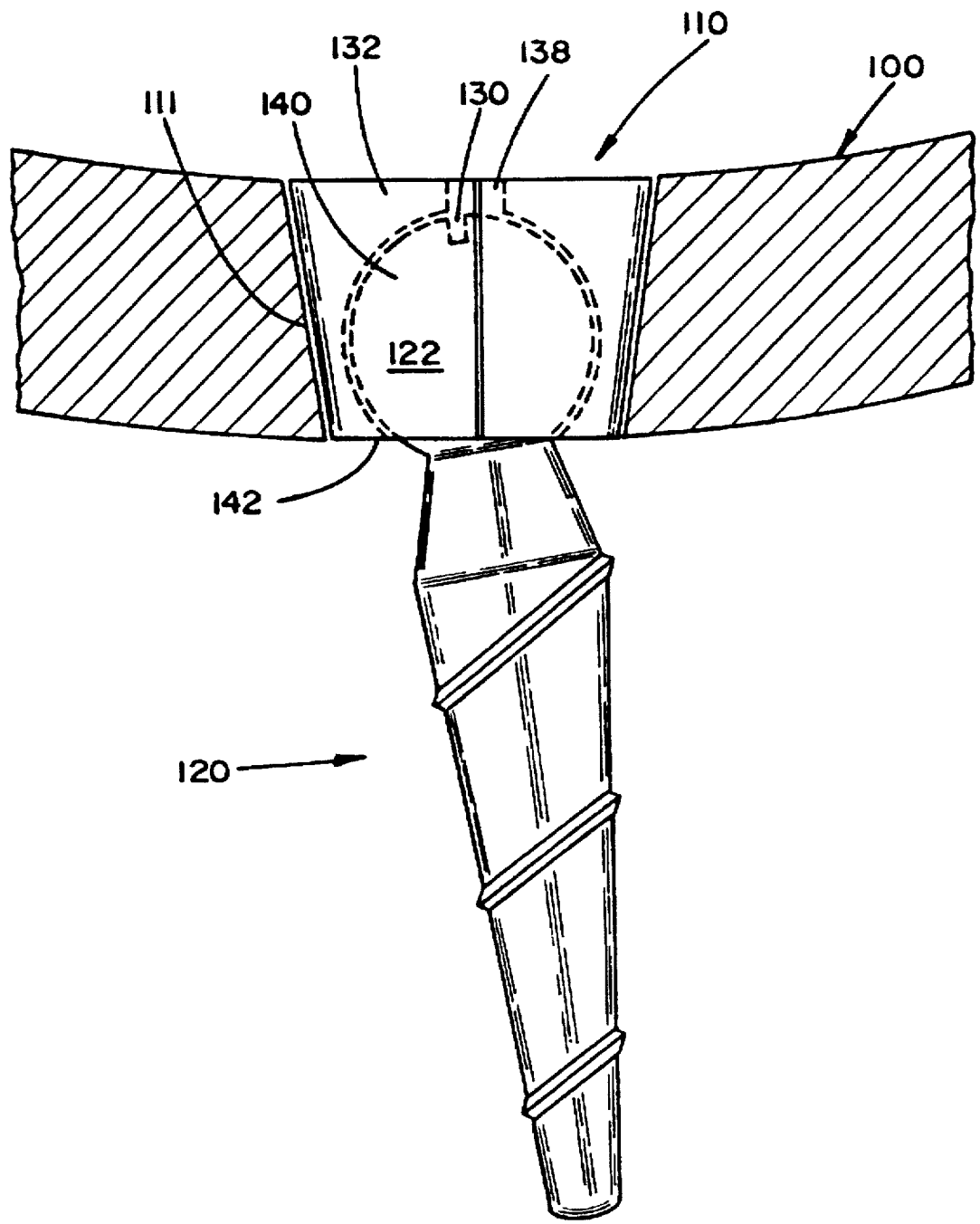
FIG. 5 is a side cross-section view of a fully assembled embodiment of the present invention.

Referring now to FIG. 5, a cross sectional view of a fully assembled embodiment of the acetabular cup 100 assembly of the present invention, is shown. With reference to the relative positions of the screw 120, hole 110, and coupling element 132, the operative steps of implanting this assembly begins with preparing the hip socket for receiving the cup 100. Next the cup 100 is positioned against the exposed socket and pre-drill holes are made into the bone at the desired insertion angle for the screws 120. Each screw 120 and corresponding coupling element 132 are then joined together so that the head 122 is within the interior volume 140, whereby the two elements are able to rotate freely with respect to one another, but are nonetheless coupled.

The recess 130 in the screw 120 and the through hole 138 of the coupling element 132 are aligned at first, and an appropriate screwdriving tool is used to insert the screw 120 through the proper hole 110 and into the pre-drilled hole in the bone. Once the screw 120 has been screwed down to the point that the bottom surface 142 of the coupling element contacts the top of the hole 110, the coupling element 132 angulates into a proper seating position. Continued insertion of the screw 120 causes the tapered surfaces 134 and 111 of the coupling element 132 and the hole 110, respectively, to engage. The taper 111 of the corresponding hole 110 causes the slot 149 to narrow, and the interior volume 140 of the coupling element to crush onto the surface of the head 122. Complete insertion of the coupling element 132 to the hole 110, locks the coupling element and screw to the cup 100, as well as locking the screw 120 and cup 100 to the bone.

Figure 6:
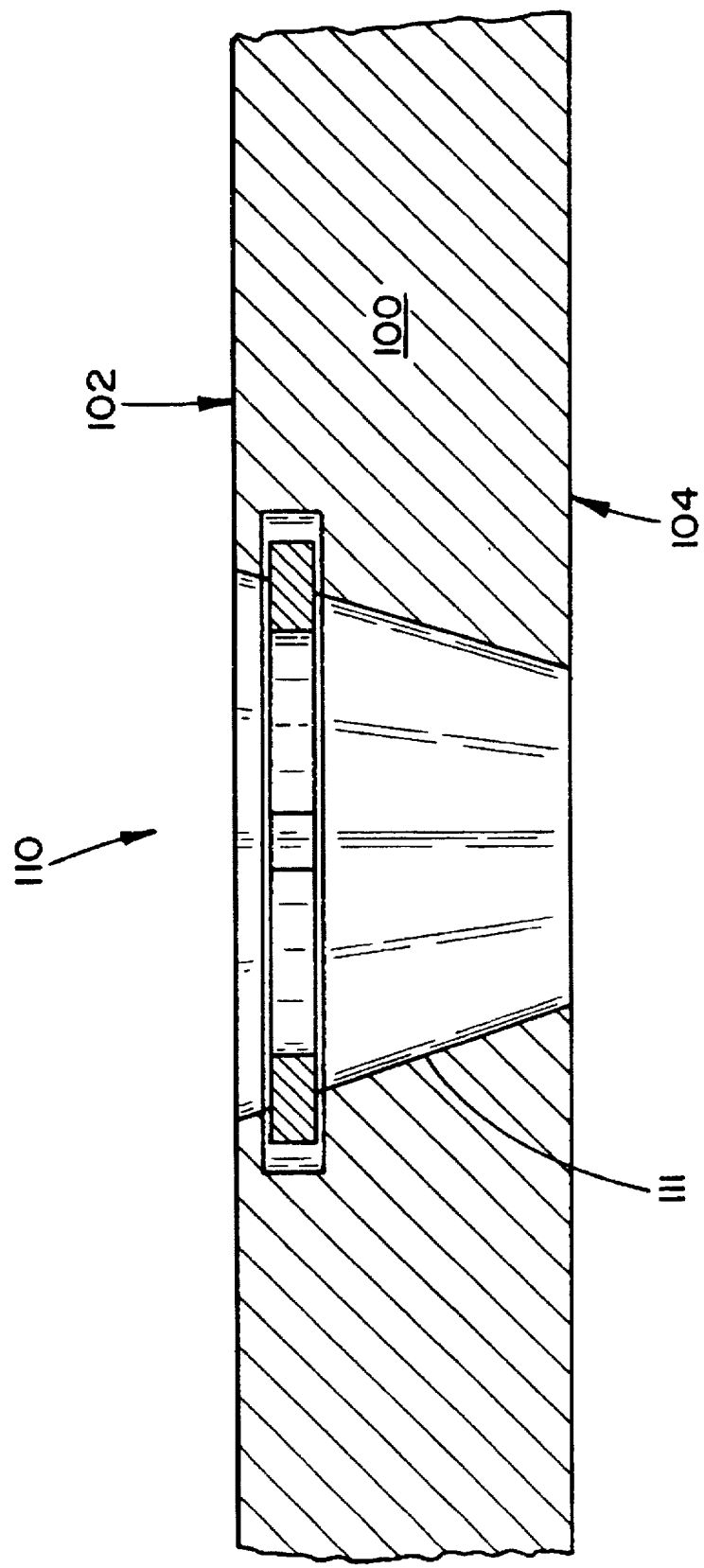
FIG. 6 is a side cross-section view of the axially tapered hole of another embodiment of the present invention, further including a retaining snap-ring.

Referring now to FIG. 6, in which a side cross-section view of a variation of the acetabular cup of the present invention is shown, the axially tapered holes 110 each further include an annular recessed channel 182. Within this annular recess 182 is provided a discontinuous "7/8ths" snap-ring 180. The undeflected outer diameter of the snap-ring is greater than the diameter of the hole 110 (so that it will remain in the recess), and the inner diameter of the undeflected snap-ring 180 is less than the diameter of the tapered hole. This permits the snap-ring 180 to protrude as an annular flange into the hole 110 in its undeflected state. The ring 180 can, however, be deflected inward or outward so as to entirely seat within the annular channel, or be removed entirely from the hole.

Figure 7:
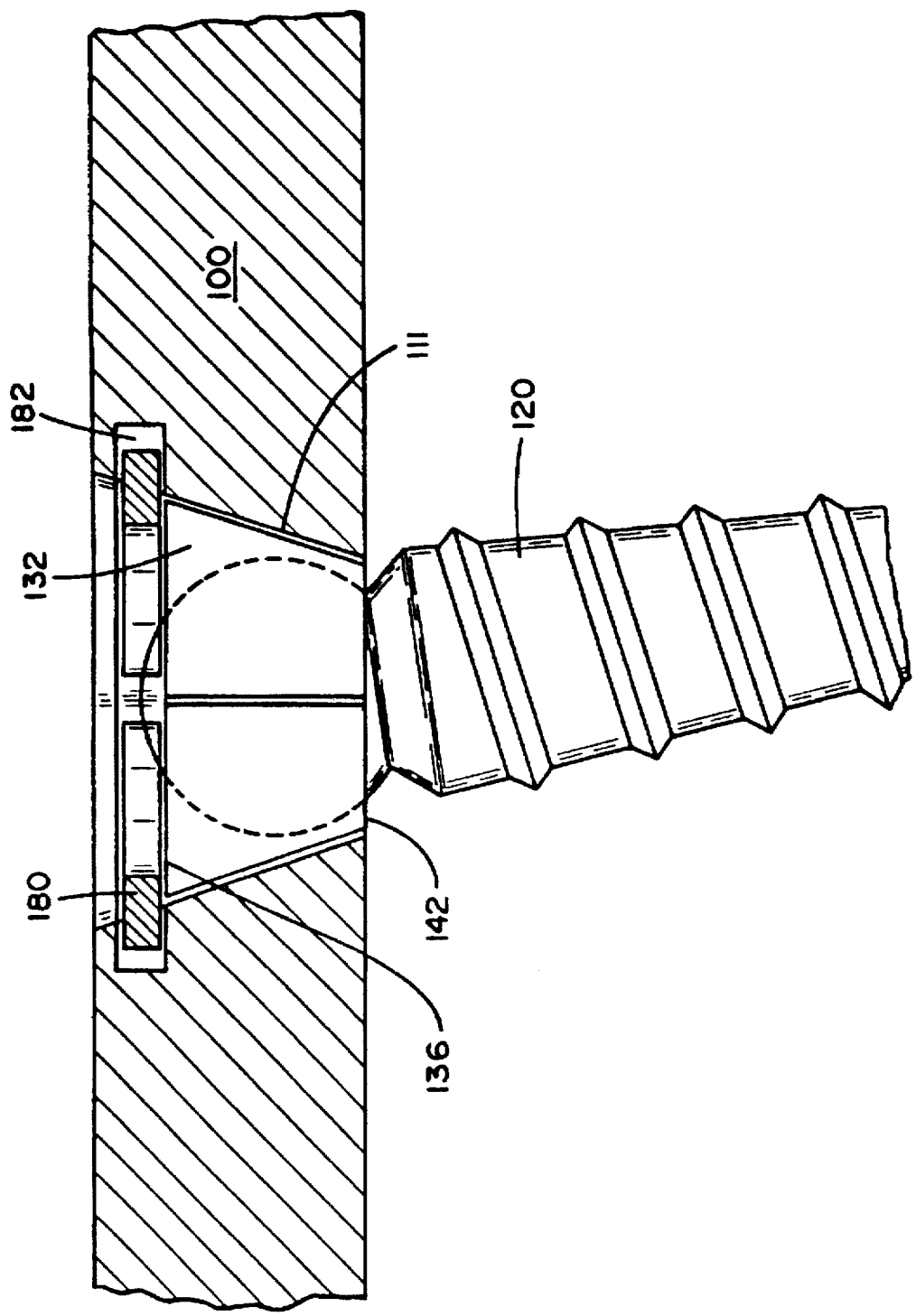
FIG. 7 is a side cross-section view of another fully assembled embodiment of the present invention.

Referring now to FIG. 7, the assembled screw 120, coupling element 132, snap-ring 180 and cup 100 are shown in a cross-section view. The snap-ring 180 is deflected inward for positioning in the recess 182. During the implantation procedure, the screw 120 and the coupling element 132 are inserted through the hole. Once the bottom 142 of the coupling element 132, respectively, seats in the top of the hole 110, and begins to travel into it, the tapered exterior surface of the coupling element 132 causes the snap-ring 180 to expand into the recess 182. Once the coupling element 132 is fully seated in the hole 110, the snap-ring 180 is freed from the outward radial pressure of the coupling element 132 and snaps back to its undeflected state. In its undeflected state it prevents the coupling element 132 from backing out of the hole 110 inasmuch as the flat upper surface 136 of the coupling element is incapable of deflecting the ring outward (it has no taper to push the snap-ring open).

While there has been described and illustrated acetabular cup devices which provide superior fixation to the hip of a patient, including polyaxial locking screws, it will be apparent to those skilled in the art that variations and modifications are possible without deviating from the broad spirit and principle of the present invention which shall be limited solely by the scope of the claims appended hereto.

We claim:

1. An acetabular cup having polyaxial locking anchoring screws for securing said cup within a recess of surrounding bone, comprising:

an acetabular cup having a plurality of through holes having a constant linear taper;

a corresponding plurality of coupling elements, each of said coupling elements being insertable into a corresponding one of said through holes; and a plurality of bone screws, each of said bone screws having a semi-spherical head portion and a shaft, said shaft portion being insertable through the corresponding through hole and into the surrounding bone, and said semi-spherical head portion being rotationally freely mounted in the coupling element prior to insertion and such that the shaft of the bone screw and the coupling element may be inserted into a corresponding through hole and said shaft of the bone screw may be inserted into the surrounding bone at a selected angle within a predetermined range of angles relative to the acetabular cup and thereby locking said coupling element and said semi-spherical head within said hole of said acetabular cup at said selected angle.

2. The acetabular cup as set forth in claim 1, wherein at least one of said plurality of through holes includes an annular recess formed in an upper sidewall portion of said hole; and further including a snap-ring being disposed in said annular recess, said snap ring deflecting outward during the insertion of the coupling element to permit the coupling element into the through hole, and said snap ring snapping back to an undeflected condition once the coupling element has fully seated in the through hole, thereby preventing the coupling element from backing out of the through hole.

3. The acetabular cup as set forth in claim 1, said acetabular cup further comprising a semi-spherical portion having an open end, and an annular flange portion extending circumferentially outward from said opening.

4. The acetabular cup as set forth in claim 3, wherein said plurality of through holes are disposed in said semi-spherical portion.

5. The acetabular cup as set forth in claim 3, wherein said plurality of through holes are disposed in said annular flange portion.

6. The acetabular cup as set forth in claim 1, wherein said coupling elements each comprise an interior semi-spherical volume, defined by a curved interior surface, which forms a receiving socket into which the semi-spherical head portion is inserted whereby the head portion of said screw is rotationally freely mounted in said coupling element.

7. The acetabular cup as set forth in claim 6, wherein said coupling element further comprises at least one slot which permits the interior semi-spherical volume to expand thereby facilitating the insertion of said semi-spherical head portion of said screw therein.

8. The acetabular cup as set forth in claim 7, wherein the corresponding through hole into which the coupling element is inserted is tapered inwardly, thereby causing, upon insertion of said coupling element into said corresponding through hole, the at least one slot to be narrow, causing the curved interior surface of the coupling element to lock the semi-spherical head portion of the screw at a definite insertion angle.

9. An acetabular cup having anchoring screws and collars for polyaxially locking said screws within axially tapered holes through said acetabular cup, comprising:

an acetabular cup having a plurality of holes therethrough said holes having a constant linear taper;

a plurality of bone screws, each having a threaded shaft and a semi-spherical head;

a corresponding plurality of coupling elements, each having an axially tapered exterior surface, said taper corresponding to the taper of the holes in said acetabular cup;

each of said coupling elements further including an interior semi-spherical volume for polyaxially retaining the semi-spherical head of said corresponding bone screw; and each of said coupling elements further including at least one axial slot formed therein, which at least one slot provides for an expansion and contraction of the interior semi-spherical volume upon the application of a radial force on the exterior surface thereof;

whereby said shaft of the bone screw may be inserted through said hole and into the bone at a selected angle within a predetermined range of angles including non-perpendicular angles relative to the tapered hole, such that upon complete insertion, the coupling element and the semi-spherical head therein are drawn into the hole, the tapered inner surface of the hole applying an inwardly directed radial force to the coupling element which is sufficient to lock the coupling element within the tapered hole, and to lock the semi-spherical head of the screw in the semi-spherical interior volume of the coupling element.

* * * * *